United States Patent [19]

Borovsky et al.

[11] Patent Number: 5,629,196
[45] Date of Patent: *May 13, 1997

[54] DNA ENCODING PEPTIDE HORMONE THAT INHIBITS DIGESTION IN INSECTS

[75] Inventors: Dov Borovsky, Vero Beach; David A. Carlson, Gainesville, both of Fla.

[73] Assignees: University of Florida Research Foundation, Gainesville, Fla.; The United States of America as represented by the Secretary of Agriculture, Washington, D.C.

[*] Notice: The term of this patent shall not extend beyond the expiration date of Pat. No. 5,439,821.

[21] Appl. No.: 468,596

[22] Filed: Jun. 6, 1995

Related U.S. Application Data

[62] Division of Ser. No. 271,698, Jul. 7, 1994, Pat. No. 5,439,821, which is a division of Ser. No. 989,290, Dec. 11, 1992, Pat. No. 5,358,934.

[51] Int. Cl.$^6$ .......................... A61K 38/04; C12N 15/11
[52] U.S. Cl. ............... 435/418; 435/419; 435/320.1; 435/235.1; 435/252.3; 435/254.2; 530/329
[58] Field of Search .................. 536/23.1; 435/320.1, 435/240.1, 240.4; 530/329

[56] References Cited

U.S. PATENT DOCUMENTS 5,011,909  4/1991  Borovsky et al. ................ 530/328
5,130,253  7/1992  Borovsky et al. ................ 435/320.1

OTHER PUBLICATIONS

Borovsky, Dov (1985) "Isolation and Characterization of Highly Purified Mosquito Oostatic Hormone" Archives of Insect Biochemistry and Physiology 2:333–349.

Borovsky, Dov (1988) "Oostatic Hormone Inhibits Biosynthesis of Midgut Proteplytic Enzymes and Egg Development in Mosquitoes" Archives of Insect Biochemistry and Physiology 7:187–210.

Borovsky, D. et al. (1990) "Mosquito oostatic factor: a novel decapeptide modulating trypsin–like enzyme biosynthesis in the midgut" FASEB J. 4:3015–3020.

Rayne, R.C., M. O'Shea (1992) "Inactivation of Neuropeptide Hormones (AKH I and AKH II) Studied In Vivo and In Vitro" Insect Biochem. Molec. Biol. 22(1):25–34.

Schwartz, J.-C. et al. (1981) "Biological Inactivation of Enkephalins and the Role of Enkephalin–Dipeptidyl–Carboxypeptidase (Enkephalinase) as Neuropeptidase" Life Sciences 29:1715–1740.

Charbonneau, Harry (1989) "Strategies for Obtaining Partial Amino Acid Sequence Data from Small Quantities (>5 nmol) of Pure or Partially Purified Protein" A Practical Guide to Protein and Peptide Purification for Microsequencing pp. 15–30.

Sober, H.A. (1968) "Handbook of Biochemistry" The Chemical Rubber Co., Cleveland, Ohio, p. C70.

Borovsky, D. et al. (1992) "Development of Specific RIA and ELISA to Study Trypsin Modulating Oostatic Factor in Mosquitoes" Archives of Insect Biochemistry and Physiology 21:13–21.

*Primary Examiner*—Robert A. Wax
*Assistant Examiner*—Einar Stole
*Attorney, Agent, or Firm*—Saliwanchik, Lloyd & Saliwanchik

[57] ABSTRACT

The subject invention concerns novel peptides which have the property of interfering with the biosynthesis of the enzyme trypsin. This property enables the use of these peptides to, for example, inhibit the formation of progeny in blood-ingesting insects, since trypsin is an essential enzyme for food digestion which provides the essential building blocks for egg development in such insects.

13 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
        Tyr  Asp  Pro  Ala  Pro
        1                   5
```

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

```
        Tyr  Asp  Pro  Ala  Pro  Pro
        1                   5
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

```
        Tyr  Asp  Pro  Ala  Pro  Pro  Pro
        1                   5
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

```
        Tyr  Asp  Pro  Ala  Pro  Pro  Pro  Pro
        1                   5
```

DNA ENCODING PEPTIDE HORMONE THAT INHIBITS DIGESTION IN INSECTS

CROSS-REFERENCE TO A RELATED APPLICATION

This application is a division of application Ser. No. 08/271,698, filed Jul. 7, 1994 now U.S. Pat. No. 5,439,821 which is a division of Ser. No. 07/989,290, filed Dec. 11, 1992, now U.S. Pat. No. 5,358,934.

This invention was made with government support under USDA Research Grant No. CRCR 1-2394. The government has certain rights in this invention.

BACKGROUND OF THE INVENTION

The existence of antigonadotropins or hormones that inhibit egg development has been demonstrated in the cockroach, eye gnat, crustaceans, house fly, and mosquitoes. Such hormones can be generally characterized as oostatic hormones. In 1985, Borovsky purified an oostatic hormone 7,000-fold and disclosed that injection of a hormone preparation into the body cavity of blood imbibed insects caused inhibition of egg development and sterility in insects (Borovsky, D. [1985] Arch. Insect Biochem. Physiol. 2:333–349). Following these observations, Borovsky, D. (1988)Arch. Ins. Biochern. Physiol. 7:187–210 disclosed that injection or passage of a peptide hormone preparation into blood sucking insects caused inhibition in the biosynthesis of serine esterase, trypsin-like and chymotrypsin-like enzymes in the epithelium cells of the gut. Since trypsin is the major proteolytic enzyme synthesized in this insect (about 70–80%), the blood meal is not digested efficiently and, consequently, free amino acids needed for the synthesis of the yolk protein synthesis in the fat body are not released into the hemolymph. Yolk protein is not synthesized and yolk is not deposited in the ovaries. The result is arrested egg development in the treated insect. The oostatic hormone peptides do not have an effect when inside the gut or other parts of the digestive system (Borovsky, D. [1988], supra).

Despite the 7,000-fold purification reported by Borovsky in 1985, the oostatic hormone was not obtained in essentially pure form and no amino acid sequence had been or could be obtained. Subsequently, the isolated peptide, trypsin modulating oostatic factor (TMOF), and two analogs of that peptide, were disclosed in U.S. Pat. Nos. 5,011,909 and 5,130,253, and in a 1990 publication (Borovsky, D., D. A. Carlson, P. R. Griffin, J. Shabanowitz, D. F. Hunt [1990] FASEB J. 4:3015–3020).

It is believed that TMOF can be rapidly inactivated in the gut of a mosquito by the action of enzymes. An endopeptidase isolated from Pseudomonas pagi (Charbonneau, H. [1989] A Practical Guide to Proteins and Peptide Purification for Microsequencing (P. T. Matsudaira, ed.), Academic Press, Inc., San Diego, Calif., pp. 15–30) was shown to hydrolyze peptide bonds on the N-terminus of Asp (D). Such an enzyme may have a role in the mosquito in regulating TMOF or its analogs by hydrolyzing the N-terminus (Tyr) from the rest of the molecule, thus inactivating the hormone. Another possibility is that the hormone may be hydrolyzed by a proline iminopeptidase-like enzyme after the hormone is cleaved, or by a pronase-like enzyme that can digest polymers of L-proline (Sober, H.A. [1968] Handbook of Biochem., The Chemical Rubber Co., Cleveland, Ohio, pp. C70). Since both the N- and C-termini of TMOF are not blocked, TMOF and its analogs could be hydrolyzed by both amino- and carboxypeptides or by endopeptidases that have been shown to play an important role in the metabolism of peptide hormones in insects and mammals (Rayne, R. C., M. O'Shea [1992] Insect Biochem. Mol. Biol. 22:24–34; Schwartz, J. C., B. Malfroy, S. De La Baume [1981] Life Sciences 29:1715–1740).

The rapid increase in pesticide resistance of disease-borne arthropods makes our hormonal approach a safer alternative to the chemical approach (e.g., synthetic pyrethroid, organochlorine, and organophosphates). However, the utility of the full-length TMOF hormone agent is limited to some extent by the rapid inactivation of this hormone by digestive enzymes.

BRIEF SUMMARY OF THE INVENTION

The subject invention concerns novel peptide hormones that inhibit digestion in pests, thus causing sterility (inhibition of egg development) in the treated pests. In a preferred embodiment, the peptides of the subject invention are used for the control of pests, such as mosquitoes, which ingest blood. The subject invention specifically exemplifies two novel peptides having the formulas:

(1) $H_2N$-YDPAP-COOH (SEQ ID NO-1) (P1); and (2) $H_2N$-YDPAP$_4$-COOH (SEQ ID NO. 4) (P4).

Both compounds have biological activity against, for example, Aedes aegypti. The novel peptides of the invention are particularly active against blood-sucking insects, particularly against species of mosquitoes such as Aedes aegypti that are potential vectors of arthropod-borne viral diseases (arboviruses). These insect species utilize serine esterases (trypsin and chymotrypsin-like enzymes) as their primary blood digesting enzymes.

The compounds of the subject invention are white powders that are highly soluble in water. They can be synthesized on a commercial peptide synthesizer. These peptides are highly stable in water solution at different pHs (5–9). Peptide (1) was allowed to stand at room temperature in solution of mosquito homogenate (including their digestive enzymes) for two weeks without loss of actMty. Thus, these peptides are particularly attractive for the control of mosquitoes and other pests. Another advantage of the penta- and octa-peptides of the subject invention is that they are more rapidly absorbed in the insect gut. Surprisingly, these short peptides are highly active. Thus, the novel peptides display a more rapid action, a decreased chance for insect gut enzymes to proteolyze the peptide, and high activity. The peptides were not affected by 1% trifluoroacetic acid and were routinely purified using this acid on HPLC.

Also included in this invention are addition salts, complexes, or prodrugs such as esters of the peptides of this invention, especially the nontoxic pharmaceutically or agriculturally acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The formulas have two weak acidic groups (carboxyl groups) on the aspattic acid (D) and on the proline (P) at the carboxyl end. Thus, esterification at these groups to form derivatives such as the methyl or ethyl esters, can be prepared by standard procedures.

The N-terminus and C-terminus of the peptides can be blocked to further inhibit proteolysis by metabolic enzymes. Derivation of peptides to block the N-terminus or C-terminus is known in the art. For example, the N-terminus can be acetylated by methods known to those of ordinary skill in the art; the C-terminus can be amidated as is well known in the art.

The novel peptides can also be synthesized wherein at least one of the amino acids is in the D-conformation, as opposed to the naturally occurring L-rotation conformation. The presence of D-conformation amino acids can inhibit the ability of proteases to degrade the peptides of the subject invention.

Also, derivation of these compounds with long chain hydrocarbons will facilitate passage through the cuticle into the pest body cavity. Therefore, a further embodiment of the subject invention pertains to compositions comprising the peptides bound to lipids or other carriers.

A further aspect of the subject invention pertains to DNA sequences encoding the peptides disclosed herein. These DNA sequences can easily be synthesized by a person skilled in the art. The sequences may be used to transform an appropriate host to confer upon that host the ability to express the novel peptides. Hosts of particular interest include bacteria, yeasts, insect viruses, and plants. For each of these hosts, the DNA sequences may be specifically designed by a person skilled in the art to utilize codons known to be optimally expressed in the particular hosts. Advantageous promoters can also easily be utilized. Bacteria, yeasts, and viruses each may be used to produce peptide for further use, or these hosts can be used as vehicles for direct application of the peptide to the target pest. Plants can be transformed so as to make the plant toxic to a target pest species which feeds on that plant. Methods for transforming plant cells utilizing, for example agrobacteria, are well known to those skilled in the art.

BRIEF DESCRIPTION OF THE SEQUENCES

Figure 1:
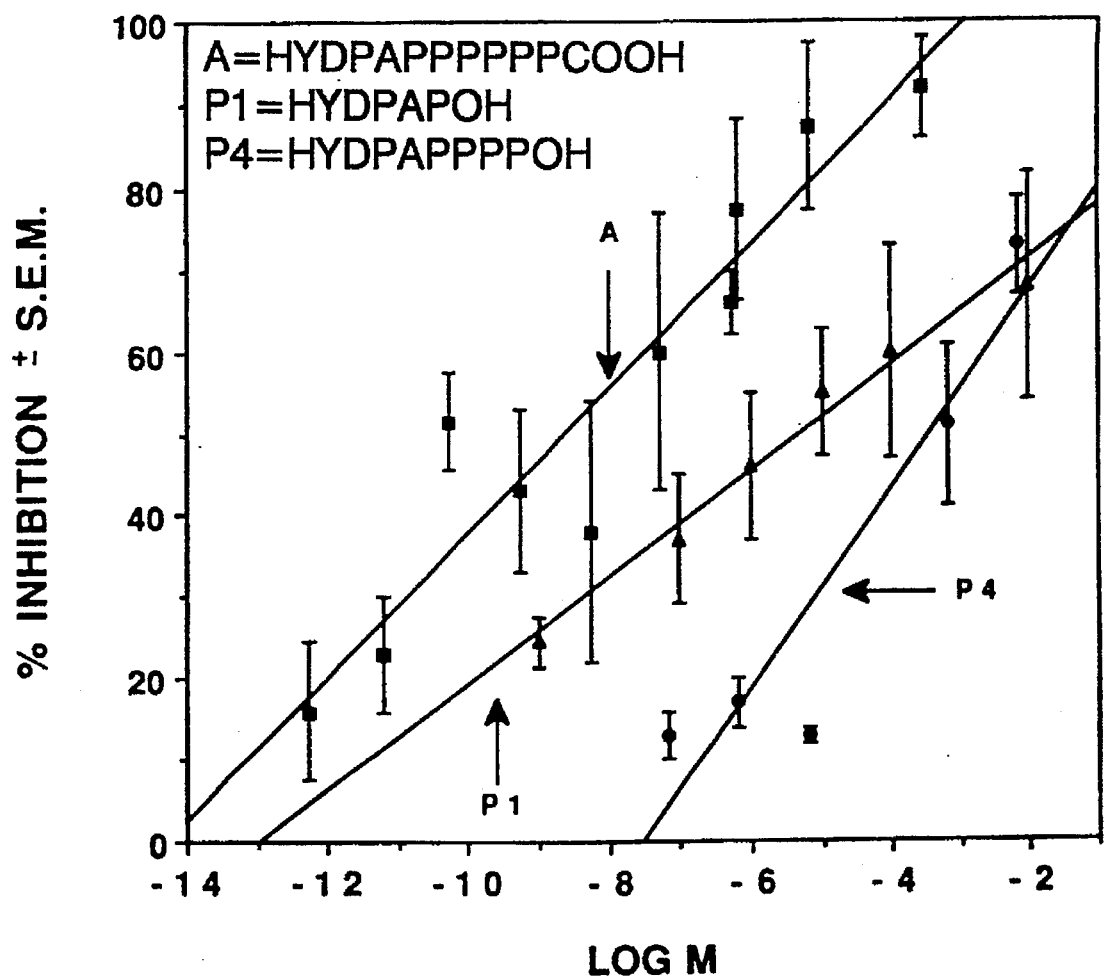
FIG. 1. Dose response curves of injections of TMOF and its analogs P1 and P4 into ligated abdomens of female A. aegypti. Each point is an average of 3–7 determinations±S.E.M.

SEQ ID NO. 1 is a novel pentapeptide according to the subject invention.

SEQ ID NO. 2 is a novel hexapeptide according to the subject invention.

SEQ ID NO. 3 is a novel heptapeptide according to the subject invention.

SEQ ID NO. 4 is a novel octapeptide according to the subject invention.

DETAILED DESCRIPTION OF THE INVENTION

The subject invention concerns novel peptides that inhibit digestion in target pests. Specifically exemplified is the use of the peptides with blood-ingesting insects such as mosquitoes. One embodiment of the subject invention is an octa-peptide, designated P4, which is a fragment of TMOF having two prolines removed from the C-terminus. This removal of two prolines amounts to a truncation of 20% of the TMOF hormone. Despite this substantial truncation, the peptide retains biological activity and has important practical advantages because it is rapidly absorbed and less susceptible to proteolysis. A second peptide of the subject invention is a fragment of only 5 amino acids of the TMOF hormone. This fragment, designated P1, has had 5 prolines removed, compared to TMOF and, thus, is only 50% of the full-length hormone. Surprisingly, as described more fully herein, this small peptide has even greater activity than the octa-peptide P4. The subject invention further encompasses the six and seven amino acid peptides, P2 and P3, (SEQ ID NOS. 2 and 3, respectively) which have 4 and 3 prolines removed, respectively. Also encompassed within the scope of this invention are other obvious modifications of these peptides.

The one-letter symbol for the amino acids used herein is well known in the art. For convenience, the relationship of the three-letter abbreviation and the one-letter symbol for amino acids is as follows:

| Ala | A | Leu | L |
| --- | --- | --- | --- |
| Arg | R | Lys | K |
| Asn | N | Met | M |
| Asp | D | Phe | F |
| Cys | C | Pro | P |
| Gln | Q | Ser | S |
| Glu | E | Thr | T |
| Gly | G | Trp | W |
| His | H | Tyr | Y |
| Ile | I | Val | V |

The novel peptides of the invention can be prepared by well-known synthetic procedures. For example, the peptides can be prepared by the well-known Merrifield solid support method. See Merrifield (1963) J. Amer. Chem. Soc. 85:2149–2154 and Merrifield (1965) Science 150:178–185. This procedure, though using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

Alternatively, these peptides can be prepared by use of well-known molecular biology procedures. DNA sequences encoding the peptides of the invention can be synthesized readily because the amino acid sequences are disclosed herein. These DNA sequences are a further aspect of the subject invention. These genes can be used to genetically engineer, for example, bacteria, insect viruses, plant cells, or fungi for synthesis of the peptides of the invention.

The insect cell line Sf9 (*Spodoptera frugiperda*), deposit number ATCC CRL 1711, is available from the American Type Culture Collection, 12301 Parklawn Drive, Rockville, Md. 20852 USA. Baculovirus *Autographa californica* nuclear polyhedrosis virus (AcNPV) is available from Texas A&M University, Texas Agricultural Experiment Station, College Station, Tex. 77843, and has been described in Smith, G., M.D. Summers (1978) Virology 89:517–527; and (1979)J. Firology 30:828–838.

Other nuclear polyhedrosis viruses (See World Health Organization Technical Report No. 531) such as *Spodoptera frumperda* (Sf MNPV), *Choristoneura furnferana* (Cf MNPV) (Smith, G., M.D. Summers [1981] J. Firol. 39:125–137), or *Spodoptera littoralis* (S1 NPV) (Harrap, K. A., C. C. Payne, J. S. Robertson [1977]Firology 79:14–31) can be used instead of *Autographa californica* NPV. Other insect cell lines can also be substituted for Spodoptera frugiperda (Sf9), for example, Trichoplusia ni (Volkman, L. E., M.D. Summers [1975]J. Firol. 16:1630-1637), *Spodoptera exigua, Choristoneura fumiferana* (Smith, G., M.D. Summers [1981]J. Firol. 39:125–137) and *Spodoptera littoralis* (Harrap, K.A. et al. [1977]Firology 79:14–31).

The various methods employed in the preparation of the plasmids and transformation of host organisms are well known in the art and are described, for example, in U.S. Pat.

Nos. 5,011,909 and 5,130,253. These patents are incorporated herein by reference. These procedures are also described in Maniatis, T., E. F. Fritsch, J. Sambrook (1982) Molecular Cloning: A Laboratory Manual, Cold Spring Harbor Laboratory, N.Y. Thus, it is within the skill of those in the genetic engineering art to extract DNA from microbial cells, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Treatment by injection of the compounds of the invention into adult female mosquitos after a blood meal stops egg development, thus rendering the female mosquito sterile and unable to reproduce. Also, using known techniques of molecular biology, mosquito larvae can be fed genetically engineered bacteria producing oostatic hormone and infect other insect larvae with bacteria or viruses containing the oostatic gene, making them unable to digest their food and subsequently starve them to death. A variety of insect viruses, including baculoviruses and entomopoxviruses, are known to those skilled in the art. The production of the claimed peptide compounds by bacteria or virus would be responsible for the starvation activity in larvae and sterilization in adults. This type of treatment of blood-ingesting insect larvae is analogous to the use of bacteria to control insect populations.

In applications to the environment of the target pest, the transformant strain can be applied to the natural habitat of the pest. The transformant strain will grow in the pest upon ingestion, while producing the peptide(s) which will have a deleterious effect on proteolytic enzymes biosynthesis and the ova. The organism may be applied by spraying, soaking, injection into the soil, seed coating, seedling coating or spraying, or the like. Where administered in the environment, concentrations of the organism will generally be from $10^6$ to $10^{10}$ cells/ml, and the volume applied per hectare will be generally from about 0.1 oz. to 2 lbs or more. Where administered to a plant part inhabited by the target insect, the concentration of the organism will usually be from $10^3$ to $10^6$ cells/cm$^2$.

In aquatic environments, insect control may be attained below the surface by varying the lipid content of the transformant microorganism strain. It is known that indigenous aquatic algae float due to their lipid content. A variation in lipid content will allow the transformant strain to be distributed at desired depths below the water surface.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the blood-ingesting insect.

Also, the genetic material of the subject invention, including nucleotide sequences of TMOF and its various analogs, can be used to transform plants, thereby conferring plant resistance to those plants. Materials and methods for transforming plant cells are well known to those skilled in the art.

MATERIAL AND METHODS

Peptides Synthesis

The novel peptides can be synthesized using standard automated solid phase peptide synthesis techniques (Barany, G., R. B. Merrifield [1979] In The Peptides, Vol. 2, Gross, E. et al., eds., Academic Press, New York, pp. 1–284), purified on $C_{18}$ reversed phase HPLC and sequenced by means of Fourier transform mass spectrometry analysis (Hunt, D.F., J.R. Yates, III, J. Shabanowitz, S. Winston, C. R. Hauer [1986] Proc. Natl. Acad. Sci. USA 83:6233–6237).

Mass Spectrometry

Mass spectra were recorded on a Fourier transform mass spectrometer operated as previously described (Hunt, D. F., J. Shabanowitz, J. R. Yates, III, N. Z. Zhu, D. H. Russell, M. E. Castro [1987] *Proc. Natl. Acad. Sci.* USA 84:620–623). Samples for mass analysis were prepared by dissolving lyophilized HPLC fractions in 5–20 µl of 5% acetic acid. A 0.5 to 1.0 µl aliquot of this solution (5–30 pmol of peptide) was then added to 1 µl matrix consisting of 1/1 glycerol/ monothioglycerol on a gold-plated, stainless-steel probe tip, 2 mm in diameter. Peptides largely in the form of $(M+H)^+$ ions were sputtered from this liquid matrix into the gas phase for mass analysis, by bombarding the sample matrix with 6–10 KeV $Cs^+$ ion projectiles. The latter were generated from a cesium ion gun (Antek, Palo Alto, Calif.) mounted directly on the spectrometer's ion source.

Methyl Ester Formation

A standard solution of 2N HCl in methanol was prepared by adding 800 µ of acetyl chloride dropwise, with stirring, to 5 ml of methanol. After 5 minutes incubation at room temperature, a 100 µl aliquot of the reagent was added to the lyophilized peptide sample. The sample was esterified for 2 hours at room temperature and the solvent removed by lyophilization.

Peptide N-Acetylation

The peptide was dissolved in 50 µl of 50 mM ammonium bicarbonate (pH 8.0) and 50 µl of freshly prepared acetylation reagent was added to this solution. Acetylation reagent was prepared by adding 100 µl of acetic anhydride to 300 µl of dry methanol and lyophilizing the mixture after allowing it to stand 15 minutes. Acetylated peptide was analyzed directly without further purification.

Manual Edman Degradation

Manual Edman degradations were performed as previously described (Tarr, G. A. [1977] In Methods in Enzymol, Enzyme Structure, Part E (Hirs, C. H. W., S. N. Timashef, eds.), Vol. 47, pp. 335, 357) and modified for use with mass spectrometry (Hunt et al. [1986], supra).

Micromanipulations

The novel peptides were dorsally injected, between the fourth and fifth abdominal segments, an hour after the blood meal by means of finely drawn capillary tube. Female mosquitoes were fed a blood meal and immediately decapitated, their abdomens ligated within an hour with a fine thread to isolate the midgut and ovaries from the brain, thorax, and corpora allata. These abdomens did not synthesize egg yolk proteins or mature their eggs. Hemolymph content of the different insects used in this study for calculation of peptide concentrations (M) were as follows: *A. aegypti* 1 hour after the blood meal, 3 µl; ligated abdomens 1 hour after the blood meal, 1.5 µl; *S. calcitrans*, 10 µl; *L anthophora*, *C. felis*, and *C. vadipennis*, 0.5 µl each. To calculate final molarity of injected peptides, these volumes were added to each injected volume (0.25 µl to 0.5 µl).

Preparation and Quantification of Proteolytic Enzymes from the Midgut

Female insects and ligated abdomens were dissected and the posterior midguts removed, washed in saline, and homogenized with a glass homogenizer in 50 mM Tris-HCl buffer (pH 7.9), containing 8 mM TPCK (chymotrypsin inhibitor). At this concentration of TPCK, no chymotrypsin activity was detected in the samples. The homogenate was centrifuged for 5 minutes at 4°C at 10,000 g, then the supernatants were collected and incubated with [1,3-$^3$H] DFP (5 μCi, spec. act. 35 Ci/mmol, Amersham, Arlington Heights, Ill.) for 18 hours at 4°C. Following incubation, [1,3-$^3$H]DIP-trypsin-like derivatives were assayed and the amount of trypsin synthesized was quantified (Borovsky, D., Y. Schlein [1988] Arch. Insect. Biochern. Physiol. 8:249–260). Chymotrypsin activity was not followed because it represented 7% of the total proteolytic activity in the midgut (Borovsky and Schlein [1988], supra). Each group of experimental animals consisted of 4 groups: (a) blood-fed, injected with a novel peptide and immediately assayed; (b) blood-fed not injected (control); (c) blood-fed injected with saline and assayed 24 hours later; and (d) blood-fed injected with a novel peptide and assayed 24 hours later. Results obtained from group (a) were considered as background and were subtracted from experimental and control groups (b), (c), and (d) and were expressed as follows:

$$\% \text{ inhibition} = \left[ 100 - \frac{(d-a)}{(c-a)} \times 100 \right]$$

Following are examples which illustrate procedures, including the best mode, for practicing the invention. These examples should not be construed as limiting. All percentages are by weight and all solvent mixture proportions are by volume unless otherwise noted.

EXAMPLE 1

Treating Mosquitos With Peptides of the Invention

To show the effectiveness of the peptides of the subject invention, we have fed female mosquitoes a blood meal, immediately ligated their abdomens, and injected different amounts of TMOF and several analogs ($3.3 \times 10^{-M}$ to $5.4 \times 10^{-13}$M). The peptides were injected into groups of ligated abdomens (3–7 groups per concentration, 2 abdomens per group). Twenty-four hours later, abdomens were assayed for trypsin-like enzyme biosynthesis.

The inhibition (%) of trypsin-like enzyme biosynthesis in the midgut was plotted against Log (M) using linear regression analysis: y=125.7+8.8 x, $r^2$=0.897, df=9, P<0.01 for TMOF(A); y=92+12.28 x, $r^2$=0.875, df=3, P<0.05 for P4; y=84+6.48 x, $r^2$=0.977, df=4, p<0.01 for P1 (FIG. 1). The ED$_{50}$ of these peptides were: TMOF $5 \times 10^{-9}$M, P1 $8 \times 10^{-6}$M, and P4 $5 \times 10^{-4}$M. Each of the peptides—TMOF, P1, and P4 demonstrated an ability to inhibit trypsin-like enzyme biosynthesis. P1 and P4 may be more stable when ingested by insects, i.e., penetrate the gut faster and thus will not be subjected to attack by peptidases as TMOF.

EXAMPLE 2

Structure of TMOF and Novel Peptides

A CPK atomic model of TMOF and a computer simulated stereoview suggests that the C-terminus of the molecule could exhibit a left-handed helical conformation in solution due to the six proline residues. The novel peptides were synthesized whereby the amino acids from the C- or N-terminus were removed or switched. Abolishing the left-handed helix at the C-terminus decreased the ED$_{50}$ of the peptides from $5 \times 10^{-4}$M to $8 \times 10^{-6}$M. Since ligated abdomens were used in these experiments, these results indicate that the secondary conformation, and not relative resistance of the hormone and its analogs to peptidases, plays an important role in the biological activity. With 6 prolines at the C-terminus, the hormone probably attains a stable left-handed helix and is fully active. However, when 2 prolines were removed, the hormone could not form a stable left-handed helix, and the 4 prolines which freely rotated hindered the binding to the cell receptor.

It should be understood that the examples and embodiments described herein are for illustrative purposes only and that various modifications or changes in light thereof will be suggested to persons skilled in the art and are to be included within the spirit and purview of this application and the scope of the appended claims.

---

We claim:

1. An isolated DNA molecule encoding a peptide having the following formula:

$$H_2N-YDPAP_n-COOH$$

where n=2 through 4.

2. The DNA molecule, according to claim 1, encoding the peptide $H_2N$—YDPAPP—COOH.

3. The DNA molecule, according to claim 1, encoding the peptide $H_2N$—YDPAPPP—COOH.

4. The DNA molecule, according to claim 1, encoding the peptide $H_2N$—YDPAPPPP—COOH.

5. A prokaryotic vector or insect virus vector comprising heterologous DNA encoding a peptide having the following formula:

$$H_2N-YDPAP_n-COOH$$

where n=2 through 4.

6. The vector, according to claim 5, wherein said peptide has the formula $H_2N$—YDPAPP—COOH.

7. The vector, according to claim 5, wherein the peptide has the formula $H_2N$—YDPAPPP—COOH.

8. The vector, according to claim 5, wherein said peptide has the formula $H_2N$—YDPAPPPP—COOH.

9. A transformed host cell comprising the DNA encoding a peptide peptide having the following formula:

$$H_2N\text{—}YDPAP_n\text{—}COOH$$

where n=2 through 4.

10. The transformed host cell, according to claim 9, wherein said peptide is H₂N—YDPAPP—COOH.

11. The transformed host, according to claim 9, wherein the peptide has the formula H₂N—YDPAPPP—COOH.

12. The transformed host cell, according to claim 9, wherein said peptide is H₂N—YDPAPPPP—COOH.

13. The transformed cell, according to claim 20, wherein said cell is a plant cell.

* * * * *

UNITED STATES PATENT AND TRADEMARK OFFICE
CERTIFICATE OF CORRECTION

Page 1 of 3

PATENT NO.    :    5,629,196

DATED         :    May 13, 1997

INVENTOR(S)   :    Dov Borovsky, David A. Carlson

It is certified that error appears in the above-identified patent and that said Letters Patent is hereby corrected as shown below:

Column 1, line 24: "Insect Blochem. Physiol." should read --*Insect Biochem. Physiol.*--;

line 26: "Ins. Biochern. Physiol." should read --Ins. Biochem. Physiol.--;

line 51: "*Pseudomonas pagi*" should read --*Pseudomonas fragi*--;

lines 62&63: "Handbook of Blochem.," should read --*Handbook of Biochem.*--

Column 2, line 38: "loss of actMty." should read --loss of activity.--;

line 56: "the aspattic acid" should read --the aspartic acid--.

Column 4: line 54: "*Spodoptera frumperda*" should read --*Spodoptera frugiperda*--;

line 54: "Choristoneura furnferana" should read --*Choristoneura fumiferana*--;

line 55: "J. Firol" should read --*J. Virol*--;

line 57: "Firology" should read --*Virology*--;

line 61: "J. Firol." should read --*J. Virol*--;

line 63: "J. Firol." should read --*J. Virol.*--;

line 64: "Firology" should read --*Virology*--.

UNITED STATES PATENT AND TRADEMARK OFFICE
CERTIFICATE OF CORRECTION

PATENT NO. : 5,629,196

DATED : May 13, 1997

INVENTOR(S) : Dov Borovsky, David A. Carlson

It is certified that error appears in the above-identified patent and that said Letters Patent is hereby corrected as shown below:

Column 6, line 40: "and lyopbilizing the" should read --and lyophilizing the--;

line 64: "S. calcitrans," should read --*S. calcitrans*--;

line 65: "*C. vadipennis,*" should read --*C. variipennis*--.

Column 7, line 15: "Insect. Biochem. Physiol." should read --*Insect. Biochem. Physiol.*--

Column 8, line 13: "inhibit trypsin-Iike" should read --inhibit trypsin-like--.

Column 9, Claim 2, line 2: --(SEQ ID NO. 2)-- was omitted;

Claim 3, line 2: --(SEQ ID NO. 3)-- was omitted;

Claim 4, line 2: --(SEQ ID NO. 4)-- was omitted;

Column 10, Claim 6, line 2: --(SEQ ID NO. 2)-- was omitted;

Claim 7, line 2: --(SEQ ID NO. 3)-- was omitted;

Claim 8, line 2: --(SEQ ID NO. 4)-- was omitted.

Column 11, Claim 9, line 2: "a peptide peptide having" should read --a peptide having--

Claim 10, line 2: --(SEQ ID NO. 2)-- was omitted

UNITED STATES PATENT AND TRADEMARK OFFICE
CERTIFICATE OF CORRECTION

PATENT NO. : 5,629,196

DATED : May 13, 1997

INVENTOR(S) : Dov Borovsky, David A. Carlson

It is certified that error appears in the above-identified patent and that said Letters Patent is hereby corrected as shown below:

Column 12, Claim 11, line 2: --(SEQ ID NO. 3)-- was omitted

Claim 12, line 2: --(SEQ ID NO. 4)-- was omitted

Claim 13, line 1: "claim 20" should read "claim 9"

Signed and Sealed this

Second Day of June, 1998

*Attest:*

BRUCE LEHMAN

*Attesting Officer*     *Commissioner of Patents and Trademarks*